US009105207B2

(12) United States Patent
Leung

(10) Patent No.: US 9,105,207 B2
(45) Date of Patent: Aug. 11, 2015

(54) FOUR DIMENSIONAL IMAGE REGISTRATION USING DYNAMICAL MODEL FOR AUGMENTED REALITY IN MEDICAL APPLICATIONS

(75) Inventor: Henry Leung, Calgary (CA)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 185 days.

(21) Appl. No.: 13/636,527

(22) PCT Filed: May 2, 2012

(86) PCT No.: PCT/US2012/036088
§ 371 (c)(1),
(2), (4) Date: Sep. 21, 2012

(87) PCT Pub. No.: WO2013/165408
PCT Pub. Date: Nov. 7, 2013

(65) Prior Publication Data
US 2013/0293578 A1 Nov. 7, 2013

(51) Int. Cl.
G06K 9/00 (2006.01)
G09G 5/00 (2006.01)

(52) U.S. Cl.
CPC .......................................... G09G 5/00 (2013.01)

(58) Field of Classification Search
None
See application file for complete search history.

(56) References Cited

U.S. PATENT DOCUMENTS

| 2003/0233039 | A1* | 12/2003 | Shao et al. ..................... 600/407 |
| 2006/0079745 | A1 | 4/2006 | Viswanathan |
| 2008/0039713 | A1 | 2/2008 | Thomson et al. |
| 2008/0123927 | A1 | 5/2008 | Miga et al. |
| 2009/0088634 | A1 | 4/2009 | Zhao et al. |
| 2011/0046476 | A1 | 2/2011 | Cinquin et al. |
| 2011/0230751 | A1 | 9/2011 | Kersting |
| 2011/0243401 | A1 | 10/2011 | Zabair et al. |
| 2012/0289825 | A1* | 11/2012 | Rai et al. ...................... 600/425 |

FOREIGN PATENT DOCUMENTS

WO 2011015822 A1 2/2011

OTHER PUBLICATIONS

International Search Report & Written Opinion dated Aug. 7, 2012 in PCT Application No. PCT/US12/26088.
Horn, B.K.P. et al., "Determining Optical Flow," Artificial Intelligence 17 (1981) pp. 185-203.

(Continued)

Primary Examiner — Nirav G Patel
(74) Attorney, Agent, or Firm — Brundidge & Stanger, P.C.

(57) ABSTRACT

Technologies described herein generally provide for an improved augmented reality system for providing augmented reality images comprising a pre-operative image superimposed on a patient image. The accuracy of registering the pre-operative image on the patient image, and hence the quality of the augmented reality image, may be impacted by the periodic movement of an organ. Registration of the pre-operative image on the patient image can be improved by accounting for motion of the organ. That is, the organ motion, which can be described by a dynamical model, can be used to correct registration errors that do not match the dynamical model. The technologies may generate a sequence of 3-D patient images in real-time for guided surgery.

20 Claims, 9 Drawing Sheets

(56) References Cited

OTHER PUBLICATIONS

Dongliang, H. et al., "Maximum Likelihood State Estimation of Semi-Markovian Switching System in Non-Gaussian Measurement Noise," IEEE Transactions on Aerospace and Electronic Systems, pp. 133-146, Jan. 2010. (Abstract only).

Low, D.A. et al., "Novel Breathing Motion Model for Radiotherapy," Int. J. Radiation Oncology Biol. Phys., vol. 63, No. 3, pp. 921-929, 2005.

Lucas, B.D. et al., "An Iterative Image Registration Technique with an Application to Stereo Vision," Proc. 7th International Joint Conference on Artificial Intelligence (IJCAI), Aug. 24-28, 1981.

Maintz, J.B.A. et al., "A Survey of Medical Image Registration," Medical Image Analysis vol. 2(1), 1998.

McClelland, J. et al., "Non-Rigid Registration Based Respiratory Motion Models of the Lung Using Two Parameters," Med. Phys. 34, 2516 (2007) (Abstract only).

Nastar, C. et al., "Frequency-Based Nonrigid Motion Analysis: Application to Four Dimensional Medical Images," IEEE Transactions on Pattern Analysis and Machine Intelligence, vol. 18, No. 11, Nov. 1996.

Pluim, J.P.W. et al., "Mutual-Information-Based Registration of Medical Images: A Survey," IEEE Transactions on Medical Imaging, vol. 22, No. 8, Aug. 2003.

Sundar, H. et al., "Estimating Myocardial Motion by 4D Image Warping," Pattern Recognition: The Journal of the Pattern Recognition Society, vol. 24, No. 11, pp. 2514-2526, Nov. 2009.

Thirion, J.P., "Image Matching as a Diffusion Process: An Analogy with Maxwell's Demons" Medical Image Analysis vol. 2, No. 3, pp. 243-260, 1998.

Wierzbicki, M. et al., "Validation of Dynamic Heart Models Obtained Using Non-Linear Registration for Virtual Reality Training, Planning, and Guidance of Minimally Invasive Cardiac Surgeries," Medical Image Analysis 8, pp. 387-401. 2004.

Yang, D. et al., "4D-CT Motion Estimation Using Deformable Image Registration and 5D Respiratory Motion Modeling," Medical Physics, vol. 35, No. 10, pp. 4577-4590, Oct. 2008.

"Kalman filter," accessed at https://web.archive.org/web/20120217133815/http://en.wikipedia.org/wiki/Kalman_filter, last modified on Feb. 16. 2012, pp. 1-15.

* cited by examiner

704 AT LEAST ONE OF

ONE OR MORE INSTRUCTIONS FOR RECEIVING A REFERENCE IMAGE OF AN ORGAN OF A PATIENT FROM A FIRST IMAGING MODALITY DEVICE;

ONE OR MORE INSTRUCTIONS FOR RECEIVING A FIRST UNREGISTERED IMAGE OF THE ORGAN USING A SECOND IMAGING MODALITY DEVICE OR THE FIRST IMAGING MODALITY DEVICE;

ONE OR MORE INSTRUCTIONS FOR DETERMINING FIRST MEASURED REGISTRATION PARAMETERS BY A SLICE-TO-VOLUME REGISTRATION OF THE FIRST UNREGISTERED IMAGE WITH THE REFERENCE IMAGE;

ONE OR MORE INSTRUCTIONS FOR DETERMINING PREDICTED REGISTRATION PARAMETERS FOR A SECOND UNREGISTERED IMAGE USING A DYNAMICAL MODEL ASSOCIATED WITH MOTION OF THE ORGAN;

ONE OR MORE INSTRUCTIONS FOR DETERMINING SECOND MEASURED REGISTRATION PARAMETERS OF THE SECOND UNREGISTERED IMAGE BY REGISTERING THE SECOND UNREGISTERED IMAGE WITH THE REFERENCE IMAGE;

ONE OR MORE INSTRUCTIONS FOR DETERMINING ESTIMATED REGISTRATION PARAMETERS OF THE SECOND UNREGISTERED IMAGE BY USING THE PREDICTED REGISTRATION PARAMETERS TO TUNE THE SECOND MEASURED REGISTRATION PARAMETERS;

ONE OR MORE INSTRUCTIONS FOR REGISTERING THE SECOND UNREGISTERED IMAGE WITH THE REFERENCE IMAGE USING THE ESTIMATED REGISTRATION PARAMETERS; OR

ONE OR MORE INSTRUCTIONS FOR GENERATING AN AUGMENTED REALITY IMAGE COMPRISING THE REFERENCE IMAGE AND THE SECOND IMAGE

FIG. 7B

FOUR DIMENSIONAL IMAGE REGISTRATION USING DYNAMICAL MODEL FOR AUGMENTED REALITY IN MEDICAL APPLICATIONS

CROSS-REFERENCE TO RELATED APPLICATIONS

The present application is a U.S. national stage filing under 35 U.S.C. § 371 of International Application No. PCT/US2012/036088, filed on May 2, 2012.

BACKGROUND

Unless otherwise indicated herein, the materials described in this section are not prior art to the claims in this application and are not admitted to be prior art by inclusion in this section.

Minimally invasive surgical procedures can offer benefits of faster healing times and less trauma to a patient. Minimally invasive surgical procedures may be carried out through a small incision or an anatomical opening of the patient. Often, various forms of surgical tools are guided through the incision or opening to perform the surgical procedure. The nature of these procedures precludes the physician from directly viewing the course of the surgical tool once the surgical tool is inserted into the patient.

An augmented reality image can aid the physician in performing the procedure. An augmented reality image may include a first image superimposed over a second image, such as a pre-operative planning image superimposed on a real-time computer generated patient image, where the latter image also depicts the surgical tool. Thus, the physician can see the surgical tool in real-time in the augmented reality image as it progresses into the patient for purposes of aiding the physician in executing the procedure.

SUMMARY

The present disclosure generally pertains to providing improved augmented reality images in terms of registration accuracy for medical applications. Improved augmented reality images may be generated by superimposing a pre-operative planning image on a real-time patient image generated by various types of imaging modality devices. Such superimposing can benefit from or in at least some cases require accurate alignment between the pre-operative planning image and the real-time patient image. The improved augmented reality image can achieve the goal of accurate and fast alignment by integrating the periodic motion exhibited by the patient as depicted in the real-time patient image into the registration process.

The present disclosure generally describes some methods for providing an augmented reality image. Some example methods may receive a reference image of an organ of a patient from a first imaging modality device. Example methods may receive an unregistered image of the organ of the patient from a second imaging modality device or the first imaging modality device. Example methods may determine predicted registration parameters for an unregistered image using a dynamical model associated with motion of the organ. Example methods may determine measured registration parameters of the unregistered image by registering the unregistered image with the reference image. Example methods may determine estimated registration parameters of the unregistered image by using the predicted registration parameters to tune the measured registration parameters. Example methods may register the unregistered image with the reference image using the estimated registration parameters. Example methods may generate, by a computer, the augmented reality image comprising the reference image and the registered image.

The present disclosure generally also describes some systems adapted to provide an augmented reality image. Some example systems may include a processor and a memory coupled to the processor. Example systems may further include an image generation module which executes in the processor from the memory and which, when executed by the processor, causes the processor to perform one or more operations. Example image generation modules may cause the processor to receive a reference image of an organ of a patient from a first imaging modality device. Example image generation modules may cause the processor to receive an unregistered image of the organ of the patient from a second imaging modality device or the first imaging modality device. Example image generation modules may cause the processor to determine predicted registration parameters for an unregistered image using a dynamical model associated with motion of the organ. Example image generation modules may cause the processor to determine measured registration parameters of the unregistered image by registering the unregistered image with the reference image. Example image generation modules may cause the processor to determine estimated registration parameters of the unregistered image by using the predicted registration parameters to tune the measured registration parameters. Example image generation modules may cause the processor to register the unregistered image with the reference image using the estimated registration parameters. Example image generation modules may cause the processor to generate the augmented reality image comprising the reference image and the registered image.

The present disclosure generally further describes some computer-readable medium having computer-executable instructions stored thereon which, when executed by a computer, cause the computer to perform one or more operations. Some example instructions may cause the computer to receive a reference image of an organ of a patient from a first imaging modality device. Example instructions may cause the computer to receive an unregistered image of the organ of the patient from a second imaging modality device or the first imaging modality device. Example instructions may cause the computer to determine predicted registration parameters for an unregistered image using a dynamical model associated with motion of the organ. Example instructions may cause the computer to determine measured registration parameters of the unregistered image by registering the unregistered image with the reference image. Example instructions may cause the computer to determine estimated registration parameters of the unregistered image by using the predicted registration parameters to tune the measured registration parameters. Example instructions may cause the computer to register the unregistered image with the reference image using the estimated registration parameters. Example instructions may cause the computer to generate the augmented reality image comprising the reference image and the registered image.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIGS. 7A and 7B are schematic diagrams illustrating a computer program product that includes a computer program for executing a computer process on a computing device;

Figure 1:
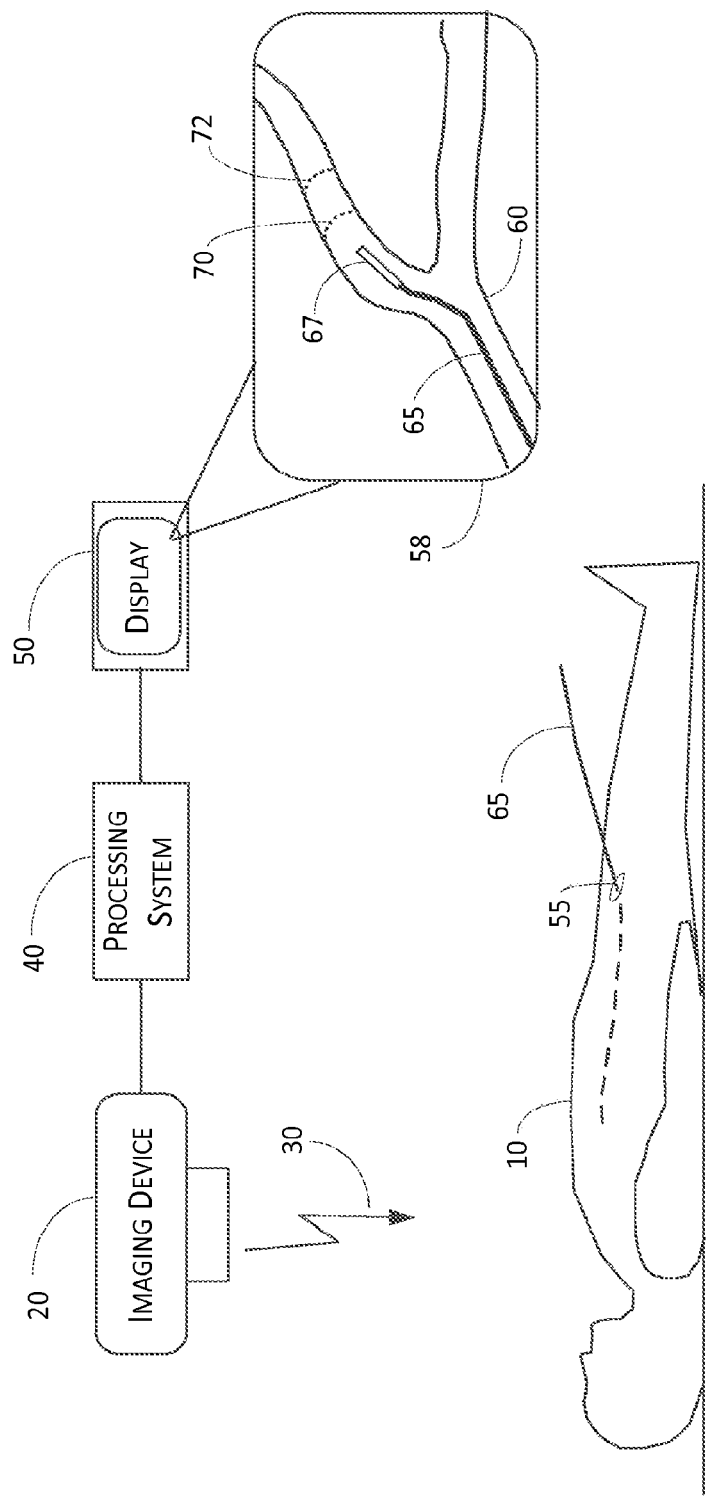
FIG. 1 depicts a schematic diagram of one context for the application of the principles disclosed herein for providing an augmented reality image involving a minimally invasive surgical procedure.

all arranged according to at least some embodiments presented herein.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description and drawings are not meant to be limiting. Other embodiments may be utilized, and other changes may be made, without departing from the spirit or scope of the subject matter presented herein. It will be readily understood that the present disclosure, as generally described herein, and illustrated in the figures can be arranged, substituted, combined, separated, and designed in a wide variety of different configurations, all of which are explicitly contemplated herein.

This disclosure is generally drawn, inter alia, to technologies adapted to provide augmented reality images for use in surgical procedures. An augmented reality image may integrate a pre-operative planning image with a real-time, computer generated image of a patient obtained using an imaging device.

A number of conventional, non-invasive imaging technologies have been developed that can be used to provide real-time patient images for use during a surgical procedure. Such images may illustrate parts of the patient not normally visible by the naked eye. Some example imaging modalities for obtaining non-invasive images may include computed tomography ("CT"), X-rays, positron emission tomography ("PET"), magnetic resonance imaging ("MRI"), and ultrasound, all of which provide various forms of non-invasive patient imaging. Some corresponding imaging devices may involve generating, for example, an electromagnetic field or X-rays, that are directed to the patient. Some other imaging devices may detect modifications to the waves or resulting electromagnetic signals and generate a virtual image of the patient. Many of these imaging technologies have been adapted to obtain, store, and process the image data as digital data so that the these patient images can be stored and manipulated by a computer processing system. Hence, the patient images are computer-generated, virtual images of the patient as opposed to being raw video obtained by a camera. The patient images may be displayed on a conventional computer display device.

A non-invasive imaging device may be adapted to obtain a single, still image or video. Video from the imaging device may be considered as a periodic sequence of images generated by the imaging device. As used herein, reference to an "image" can refer to a single image or a video. The rate of the periodic sequence of images generated by the imaging device may vary. For example, while a conventional digital video camera may produce video at a rate of 60 images per second, a non-invasive imaging device may produce images at a slower rate. The time between updated images for a non-invasive imaging device may vary based on the needs of each surgical procedure. An inter-frame time period (i.e., an amount of time elapsed before a new real-time or near real-time image is generated) may range from about a fraction of a second to about a second or two, according to some implementations.

As used herein, the term "real-time" with respect to an image may refer to an image captured and delivered in real-time or near real-time. For example, real-time imaging technologies may experience delays in processing or transmission. Such delays may cause an intended real-time image to be near real-time in practice.

As is known in the art, prior to performing the surgical procedure, the physician may obtain pre-operative planning images of the patient to aid in planning the surgical procedure. These pre-operative planning images are referred to herein as patient planning images and may be obtained using the same imaging device that obtains the real-time patient image. Further, the physician may annotate a patient planning image to describe aspects of the planned surgical procedure. For example, the physician may indicate a line on the patient planning image depicting where an incision or cut is to be made on the patient. This line can be generated in different ways, including by the physician using a computer aided graphics tool for indicating the line over the patient planning image. This line, excluding the patient planning image, is one form of what is termed herein as a pre-operative planning image.

A conventional augmented reality image for a surgical procedure may include a first image superimposed on a second image. In some applications that use augmented reality images, the first image may be the pre-operative planning image, such as the above mentioned line, superimposed on the second image that may be the real-time patient image. The real-time patient image is obtained during the surgical procedure and may be a conventional non-invasive image obtained from an imaging device, which may be the same imaging device used to obtain the patient planning image. In other cases, the real-time imaging device may be of a different device or modality than the pre-operative planning imaging device.

The conventional augmented reality image may be referenced by the physician while performing the minimally invasive surgery. The physician may insert a surgical tool into an incision of a patient, and the surgical tool may appear on the real-time patient image. Once the surgical tool is inserted, the physician may not be able to readily observe the progress of the surgical tool inside the patient using the naked eye. However, the conventional augmented reality image may provide the physician with the position or orientation of the surgical tool, or to enhance the location of a tumor.

The physician may reference the patient planning image during the surgical procedure, but that image was obtained in a pre-operative planning stage. Thus, the patient planning image may not indicate the relative location of the surgical tool in the patient during the surgical procedure. As a result, the patient planning image may provide little or no help to the physician while the surgical procedure is being performed.

In contrast, a conventional augmented reality image that incorporates a real-time patient image may provide the physician with the relative location of the surgical tool in the patient as the procedure is performed. In order to further aid the physician during a surgical procedure, an image processing system may generate an augmented reality image by superimposing the pre-operative planning image on the real-time patient image. The augmented reality image may aid the physician in the placement of the surgical tool with respect to the planned procedure because the physician may see the previously defined pre-operative planning information (e.g., defining where the physician intends to make a cut) superimposed on the real-time patient image.

However, conventional augmented reality may perform registration of the pre-operative planning image and the real-time patient image without taking into account the effect of real-time movement, such as movement caused by cardio or respiratory motion, on the real-time patient. As a result, conventional augmented reality may inaccurately superimpose the pre-operative planning image onto the real-time patient image due to registration errors. By taking real-time patient movement as prior information to perform registration, a more accurate augmented reality image may be generated for the physician.

Turning now to the figures, FIG. 1 depicts a schematic diagram of one context for the application of the principles disclosed herein for providing an augmented reality image involving a minimally invasive surgical procedure taking into account motion exhibited by the patient, arranged in accordance with at least some embodiments presented herein. In FIG. 1, a patient 10 may be undergoing a minimally invasive surgical procedure involving the heart. The exact surgical procedure may vary, but for purposes of illustration, the procedure may involve insertion of a surgical tool into a vein at an incision in the patient's leg. The surgical tool may then be guided through the vein to the patient's heart. Specifically, the surgical tool may be attached to a guide wire 65 that is inserted into an incision 55 in the patient 10.

An imaging device 20 may be used to obtain real-time patient image or images during the surgical procedure. The imaging device 20 may have been used to obtain the aforementioned patient planning images. Some examples of the imaging device 20 may include an MRI imaging device, a CT imaging device, or an ultrasound imaging device. The MRI imaging device may analyze radio frequency signals generated as a result of a changing magnetic field directed to the patient 10. The CT imaging device may obtain and analyze X-ray images. The ultrasound imaging device may generate acoustical waves and analyze reflections caused by the acoustical waves. The imaging device 20 may generate real-time image data using an imaging processing system 40.

The imaging processing system 40 may also store the pre-operative planning image and may generate an augmented reality image 58 on a display 50 by superimposing the pre-operative planning image on the real-time patient image. The display 50 showing the augmented reality image 58 may be viewable as the physician performs the procedure. Since the physician may not be able to view the surgical tool with the naked eye once the surgical tool is inserted into the patient 10, the physician may view the augmented reality image 58 to aid in guiding the surgical tool. The augmented reality image 58 illustrates the surgical tool 67 attached to the end of the guide wire 65 that is guided through a vein 60.

The augmented reality image 58 may include a pre-operative planning image that includes two lines 70, 72, which are superimposed on the real-time patient image depicting the vein 60 and guide wire 65, to inform the physician of the area involving the procedure. The lines 70, 72 may indicate, for example, a location where a stent should be placed in the vein 60 or where a tumor should be excised.

The vein 60 may be located on, or nearby to, the patient's heart. Thus, the vein 60 may be periodically moving as a result of the heart's beating action. The periodic movement reflected on the real-time patient image of the augmented reality image 58 could be significant with respect to the positioning of the lines 70, 72 in the augmented reality image 58. Such movement may cause the lines 70, 72 to be misaligned with respect to the vein 60 in the augmented reality image 58. In order to address this potential misalignment, the pre-operative planning image, including lines 70, 72 should move in a manner corresponding to the movement of the real-time patient image.

The accuracy of superimposing the pre-operative planning image over the real-time patient image may affect whether the physician can utilize the augmented reality image to properly execute the procedure as planned. For example, if the procedure involves placing a stent at the location indicated by the lines 70, 72, and the lines are not accurately positioned on the real-time patient image, then the augmented image may misinform the physician executing the procedure.

Aligning the pre-operative planning image with the real-time patient image may involve a process known as registration. Superimposing the pre-operative planning image with the real-time patient image may involve aligning certain readily distinguishable points on the pre-operative planning image and the real-time patient image. These points may be interchangeably referred to as "landmark points," "registration points," or "control points." A control point may be any easily distinguishable or identifiable point on an image. For example, a control point can represent an apex point where an outline is convex or concave. In some implementations, two or more control points may be used to register the pre-operative planning image with the real-time patient image.

In some examples of augmented reality images, a pre-operative planning image is superimposed on the real-time patient image, where the real-time patient image depicts a stable structure. For example, the pre-operative planning image may represent a cut line superimposed on the real-time patient image of a bone, which may be in the patient's leg. The bone by itself is fairly stable and may not exhibit any periodic movement. As a result, alignment of the cut line to the real-time patient image of the bone may be relatively straightforward.

In some other examples of augmented reality images, a pre-operative planning image is superimposed on a real-time patent image, where the real-time patient image depicts a structure, such as an organ, that exhibits movement. Here, registration of the pre-operative planning image on the real-time patient image may be more complicated due to the movement of the structure. For example, if the surgical procedure involves the heart or a lung, movement may be expected. In the case of a surgical procedure involving the patient's lung, breathing may be voluntarily suspended by a patient for a limited amount of time in certain cases (e.g., the physician may request that the patient hold her breath). However, the suspension of breathing is possible only if the patient is conscious, and is only temporary. Normal movement of the lung will return when the patient's respiration returns to normal. Registration of the pre-operative planning image to a moving real-time patient image may require adapting the pre-operative planning image to the real-time patient image to reflect motion of the organ.

The augmented reality image in FIG. 1 is illustrated in a two-dimensional format for simplicity. In many applications, the augmented reality image can be more complex. For example, the surgical procedure could involve excising tumor tissue from a lung, where the tumor has a three-dimensional shape. The shape of the tumor to be excised could be enhanced on the real-time patient image by using a pre-operative planning image illustrating the shape of the tumor. The pre-operative planning image illustrating the shape of the tumor on the lung may be superimposed on the real-time patient image of the lung, which also may be in three-dimensions.

Figure 2A:
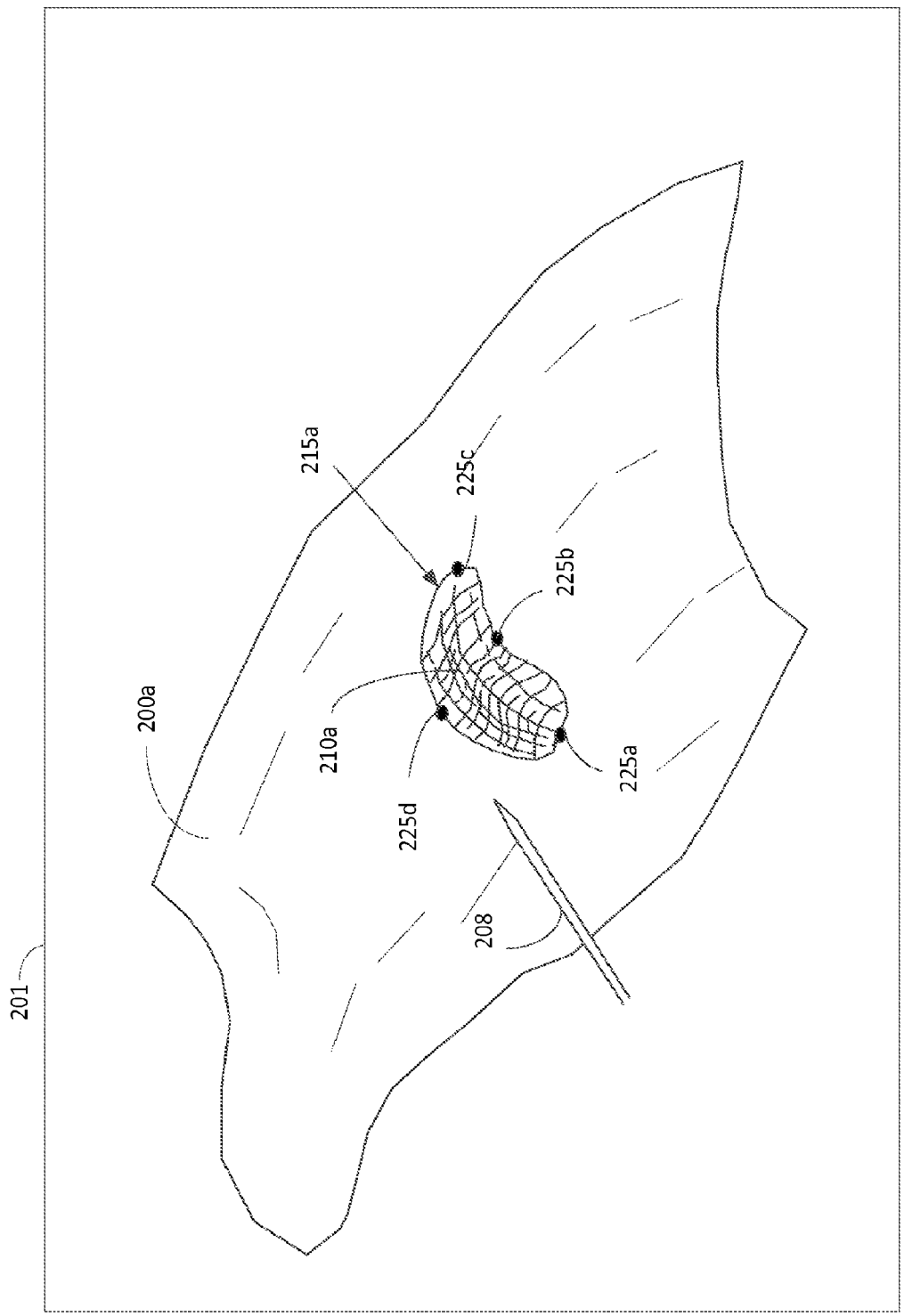
FIGS. 2A and 2B diagrammatically illustrate a pre-operative planning image superimposed on a real-time patient image of an organ exhibiting movement.
Figure 2B:
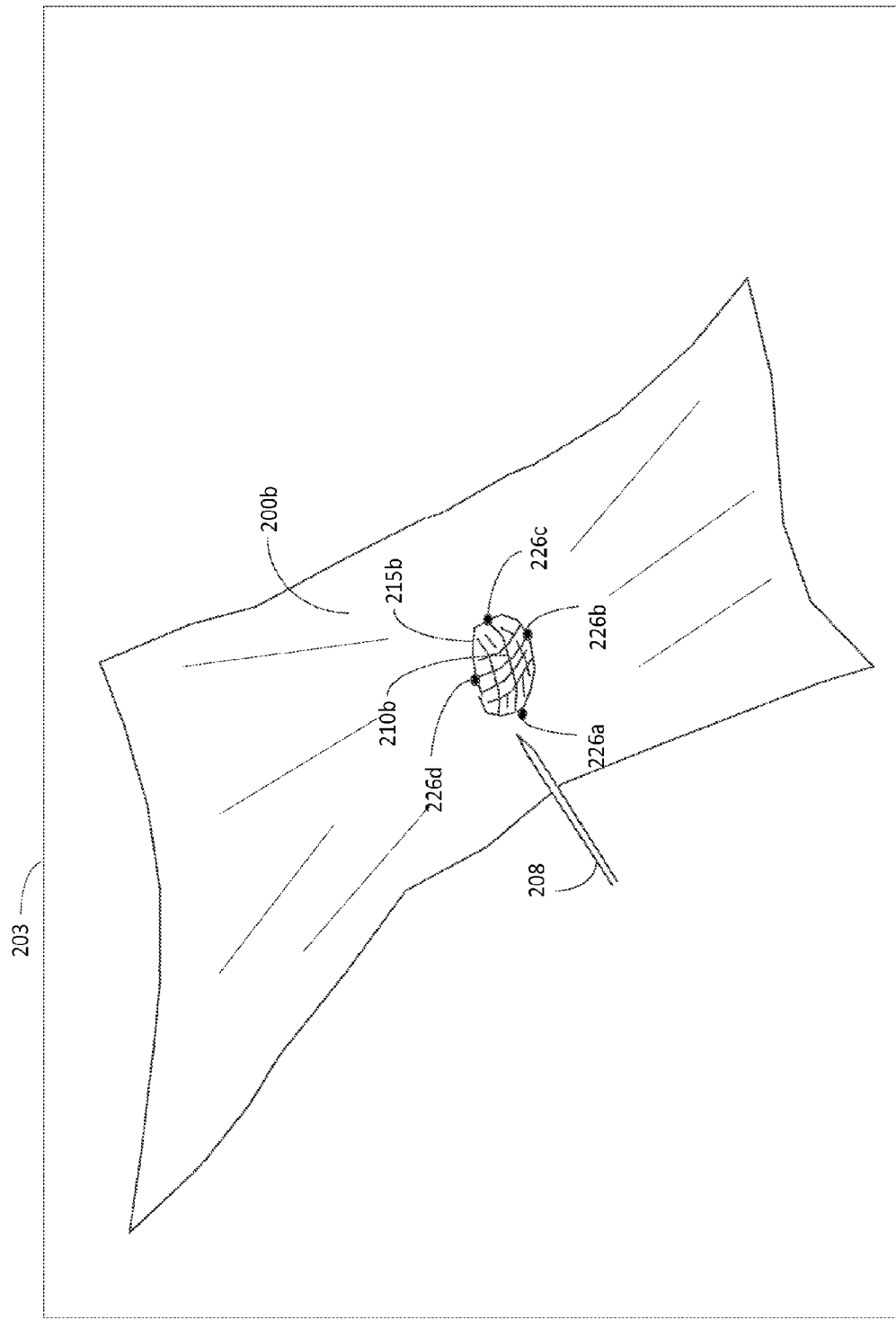

This example is illustrated in FIGS. 2A and 2B. FIGS. 2A and 2B diagrammatically illustrate a pre-operative planning image superimposed on a real-time patient image of an organ exhibiting movement, arranged in accordance with at least some embodiments presented herein. FIG. 2A illustrates an augmented reality image 201 depicting a portion of a lung in a first state 200a in three dimensions. Superimposed on the augmented reality image 201 of the lung is a wireframe pre-operative planning image in a first state 210a. The wireframe pre-operative planning image in the first state 210a may depict the shape and outline of a tumor in a first state 215a. In this depiction, the tumor in the first state 215a has a kidney-shaped outline that matches the outline of the wireframe pre-operative planning image in the first state 210a. The outline of the tumor in the first state 215a may have been determined in a patient pre-operative planning image obtained earlier, and the wireframe pre-operative planning image in the first state 210a may have been previously defined by the physician to indicate, for example, an outline for excising the tumor in the first state 215a during a surgical procedure.

FIG. 2A may represent the shape and position of the lung and the tumor at a given time, which may be referred to as t=T. That is, when t=T, the lung may have a shape and position corresponding to the first state 210a, and the tumor may have a shape and position corresponding to the first state 215a. The outline of the tumor in the real-time patient image may not be clearly demarked or readily discernible by the physician during the procedure. As a result, the superimposed pre-operative planning image in the first state 210a may be used to guide the physician during the procedure. The imaging processing system 40 may define and use a series of control points 225a-225d for registering the wireframe pre-operative planning image in the first state 210a on the tumor in the first state 215a of the real-time patient image. In particular, the imaging processing system 40 may register the control points 225a-225d on the wireframe pre-operative planning image in the first state 210a with corresponding control points on the real-time patient image. An example of this registration process is described in greater detail below with reference to FIG. 4.

The augmented reality image of FIG. 2A also depicts a surgical tool 208 positioned adjacent to the tumor. The depiction of the surgical tool 208 may be part of the real-time patient image, not the wireframe pre-operative planning image.

The lung may be exhibiting movement due to normal aspiration, which results in the tumor changing shape or position over time. In FIG. 2B, an augmented reality image 203 of the lung in a second state 200b is shown in a contracted state at t=T+1. The lung in the second state 200b may exhibit a different shape or position at this time from the lung in the first state 200a. The contracted state of the lung in the second state 200b may also cause the shape or position of the tumor to transition from the first state 215a to a second state 215b. The change in shape or position of the tumor from the first state 215a to the second state 215b may also cause a corresponding change in shape or position of the wireframe pre-operative planning image from the first state 210a to a second state 210b.

The imaging processing system 40 may alter the wireframe pre-operative planning image to correspond to the new shape or position of the tumor in the second state 215b. The wireframe pre-operative planning image may depict four control points 226a-226d that correspond to the four control points 225a-225d of FIG. 2A, but the movement of the lung may result in a different relative positioning of the control points 226a-226d with respect to the control points 225a-225d. By monitoring the change in positions between the control points 225a-225d and the control points 226a-226d, the imaging processing system 40 may adjust the shape or position of the wireframe pre-operative planning image from the first state 210a to the second state 210b. The movement of the lung between the first state 200a and the second state 200b may also change the relative position of the tumor with respect to the surgical tool 208.

The augmented reality images depicted in FIG. 2A and FIG. 2B may be three dimensional images where shapes corresponding to the real-time patient image may vary with time. Hence, in some implementations, the augmented reality images 201, 203 can be described as a four-dimensional ("4-D") image, where the fourth dimension is time.

It may be desired to ensure that the pre-operative planning image, whether it be the wireframe pre-operative planning image in the first state 210a at t=T shown in FIG. 2A or the wireframe pre-operative planning image in the second state 210b at t=T+1 shown in FIG. 2B, is properly registered with the corresponding real-time patient image at the time. To register the pre-operative planning image with the real-time patient image, the control points may be used to map or register the pre-operative planning image to the real-time patient image.

Figure 3:
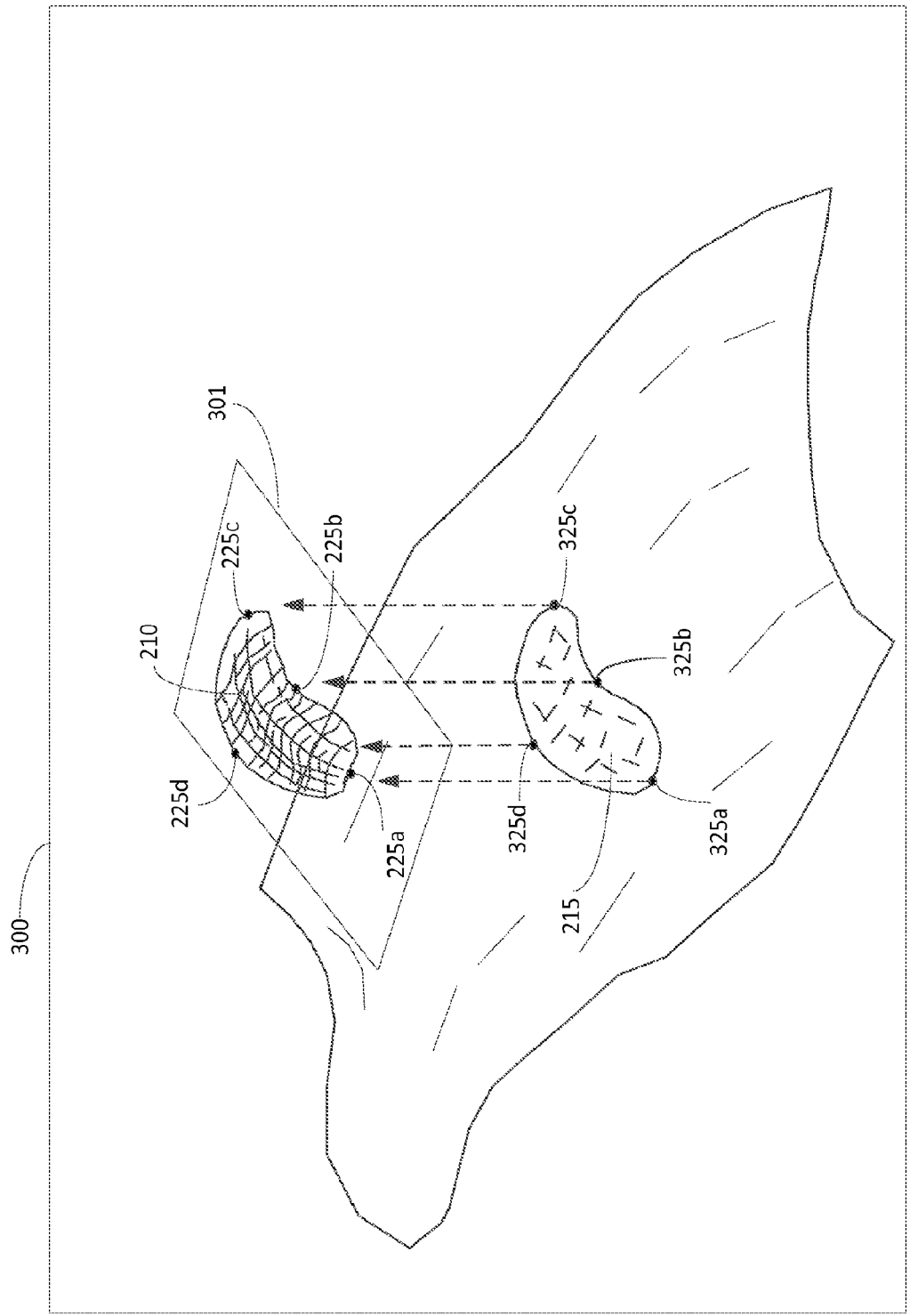
FIG. 3 is an illustration of registering a pre-operative planning image on a real-time patient image using control points.

FIG. 3 is an illustration of registering a pre-operative planning image 210 on a real-time patient image 300 using control points, arranged in accordance with at least some embodiments presented herein. In FIG. 3, the real-time patient image 300 may depict a tumor 215 by means of anomalies in the lung tissue. The tumor 215 is diagrammatically shown in FIG. 3 using short lines. The real-time patient image 300 of the tumor 215 may not provide a clear demarcation of the tumor 215 to the physician. Hence, superimposing the pre-operative planning image 210 on the real-time patient image 300 can provide a clear demarcation of the tumor 215 to the physician during the procedure.

Image processing software can be used to process the real-time patient image 300 to identify the control points 325a-325d of the tumor 215 and the corresponding control points 225a-225d of the pre-operative planning image 210. The depiction in FIG. 3 illustrates the concept of registration, not necessarily the resulting augmented reality image. More specifically, the resulting augmented reality image may instead present the pre-operative planning image 210 superimposed on the real-time patient image 300 such as shown in FIG. 3.

Image registration for 4-D images may be performed in the following manner for a particular two-dimensional image ("2-D") image (called a "slice") by registering the 2-D image with another 2-D image and performing the registration repeatedly for different slices of a three dimensional ("3-D volume"), and again at different points in time. This approach is termed a "slice-to-slice" registration, because this approach aligns a 2-D image with a 2-D image.

Another form of image registration involves registering a 2-D image with a 3-D image, which is referred to as a slice-to-volume registration. A 3-D volume can be modeled as a number of 2-D layers stacked upon each other. A slice-to-volume registration involves mapping a particular 2-D image to one of the various stacked layers in a 3-D volume to determine which layer in the volume is the most appropriate match. Still another form, as shown in FIGS. 2A and 2B, is a volume-to-volume registration and may involve registering a 3-D volume to a 3-D image.

The registration process can occur by defining a transformation function for aligning the pre-operative planning image 210 with the real-time patient image 300. The transformation function can be a static transformation function if the real-time patient image 300 is not moving. A static transformation function could be used for a sequence of patient images, but the processing for aligning the pre-operative planning image 210 and the real-time patient image 300 may be determined anew for each new real-time patient image. If the real-time patient image 300 reflects a periodic movement, then incorporating the time dimension into the transformation process may result in a faster and more accurate registration.

In other words, the slice-to-slice or slice-to-volume registration can be repeated as needed for each time instance using a static transformation function. However, this approach may involve significant processing, mainly from searching proper control point pairs for both images, which militates against providing fast and frequent updates to the real-time augmented reality images. Specifically, registering the pre-operative planning image 210 in this manner for a time varying real-time patient image 300 may not take advantage of the periodic aspect of the motion that is being exhibited by the real-time patient image 300. In many instances, the real-time patient image 300 may depict a lung or heat, and its motion may be well known and mathematically modeled. Applying a motion model of the organ can achieve a faster and more accurate registration of the pre-operative planning image 210 and the real-time patient image 300.

Knowledge of a motion model can be used to determine registration parameters which define how the image pixels change in position with respect to time. Determining how the image pixels change in position over time may involve an analysis of sequential real-time images obtained from the patient. For reference purposes herein, the pre-operative planning image 210 may also be termed the "reference image" and the real-time patient image 300 may also be termed an "unregistered" image.

Figure 4:
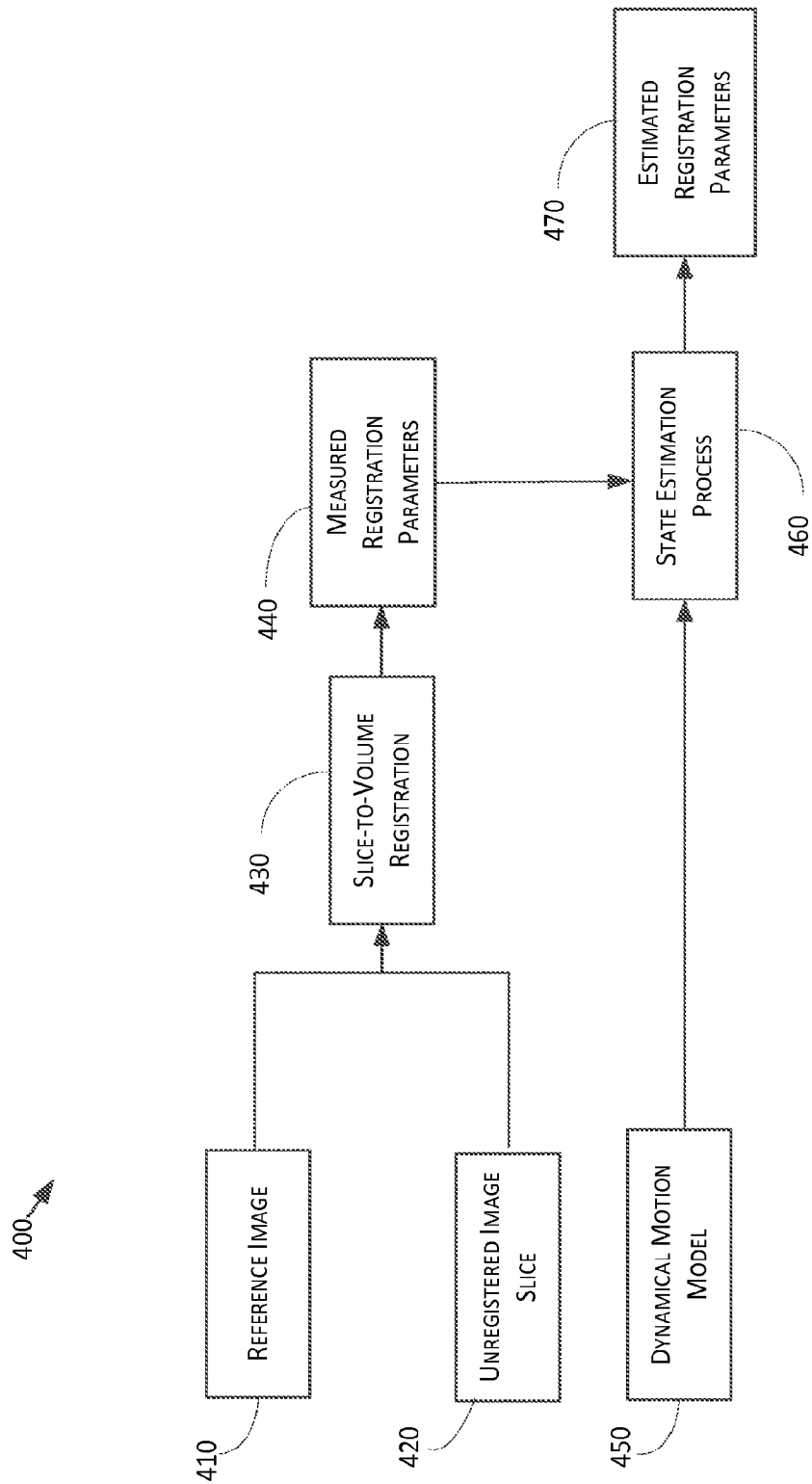
FIG. 4 is a diagram illustrating an example process flow to determine estimated registration parameters.

FIG. 4 is a diagram illustrating an example process flow 400 to determine estimated registration parameters, which can then be used to facilitate registration, arranged in accordance with at least some embodiments presented herein. The process flow 400 may involve obtaining a reference image (410) that can be the pre-operative planning image developed in the pre-operative planning process. An unregistered image slice (420) may be the real-time patient image obtained from the various imaging modality devices previously mentioned.

The unregistered image slice (420) as well as the reference image (410) in a memory of an image processing system may be used to perform a slice-to-volume registration (430) using any of the conventional techniques known in the art. In other embodiments, a slice-to-slice or volume-to-volume registration may be performed.

The slice-to-volume registration can be performed using techniques such as the optical flow method by Horn and Schunck (B. K. P. Horn and B. G. Schunck, "Determining Optical Flow," Artificial Intelligence, vol. 17, pp. 185-203, 1981, the contents of which are incorporated by reference). It can also be performed using the least-mean square optical flow method by Lucas and Kanade (B. D. Lucas and T. Kanade, "An Iterative Image Registration Technique With An Application To Stereo Vision," Proceedings of the 7$^{th}$ International Joint Conference on Artificial Intelligence, pp. 674-679, 1981, the contents of which are incorporated by reference). It can also be performed using the algorithm by Thirion (J. P. Thirion, "Image Matching As A Diffusion Process: An Analogy With Maxwell's Demons," Med. Image Analysis, vol. 2, pp. 243-260, 1998, the contents of which are incorporated by reference).

The slice-to-volume registration may result in a set of measured registration parameters 440 at the time instant t, denoted as R(t). R(t) is a parameter vector that defines the transformation of the image pixels or the control points. The transformation may be a rigid transformation and if so, then R(t) may contain six parameters, i.e., three translation parameters along the x, y, and z axis, and three orientation parameters around the x, y, and z axis. The registration parameter vector may define how the image pixels or the control points are transformed in the coordinate space from unregistered image to reference image.

Once the measured registration parameters are obtained, the measured registration parameters may be used as an input to a state estimation process (460) to determine the estimated registration parameters (470) at the time instant t. The state estimation process (460) may use another input that is the dynamical model (450) associated with the motion of the patient's organ. The dynamical model (450) can be expressed as the following two equations, equation (1) and equation (2) shown below, which are interrelated with the registration parameter vector:

$$\rho(t)=F(\rho(t-1))+w(t) \qquad \text{eq. (1)}$$

$$R(t)=H(\rho(t))+v(t) \qquad \text{eq. (2)}$$

In equation (1), ρ(t) is a vector of the true registration parameters at a given time instant t. The "true" registration parameters may refer to those parameters that are obtained under the assumption that the real-time patient image and the pre-operative planning image are both clean images without any noise corruption or distortion. However, as well known, both images may not be clean due to many reasons, such as the noise of the imaging device, the illumination noise, the lens distortion, etc. Hence, the "true" registration parameters may not be practically reached; rather the "true" value can be determined as close as possible by statistical means.

The function F is the state transition function that describes the dynamics of the registration parameters under the patient's motion and w(t) is a transition noise value that accounts for imperfect motion of organs (e.g., the tidal volumes may usually take different values even though they are measured at full exhalation or full inhalation). Thus, equation (1) states that the registration parameters at a given time can be determined by the state transition function applied to the registration parameters at the previous time instant added to the state transition noise.

The state transition function F can be obtained from a motion estimation method for the specific organ involved. For example, if the organ is a lung, the motion model used can that be described by Low (D. A. Low, P. J. Parikh, W. Lu, J. F. Dempsey, S. H. Wahab, J. P. Hubenschmidt, M. M. Nystrom, M. Handoko, and J. D. Bradley, "Novel Breathing Motion Model For Radiotherapy," Int. J. Radiat. Oncol., Biol., Phys., vol. 63, pp. 921-929, 2005, the contents of which are incorporate by reference). Alternatively, the algorithm proposed by McClelland can be used (J. McClelland, J. Blackall, S. Tarte, S. Hughes, and D. Hawkes, "Non-rigid Registration Based Respiratory Motion Modules of the Lung Using Two Parameters," Med. Phys., vol. 34, 2007, the contents of which are incorporated by reference). Further motion models for the organ may be used as developed. In other embodiments, motion of the heart, tissues, or other organs may be used for the function F.

As state above, R(t) in equation (2) is the measured parameter vector at the time t. H is a measurement function of $\rho(t)$, and v(t) is a measurement noise at time t that accounts for imperfect imaging or imperfect registration schemes. Thus, equation (2) states that the measured parameter vector at time t is a measurement function applied to the true registration parameters at time t plus the measurement noise.

The state estimation process (460) can then use a Kalman filter process if the process noise (w(t)) is white Gaussian noise with a zero mean. If the process noise is non-Gaussian noise, then the state estimation process (460) can be achieved by employing an expectation-maximization approach. Both the Kalman filter process and the expectation-maximization approach are known to those skilled in the art. Background information on the Kalman filtering process can be found, for example, in the reference entitled: Kalman Filter, Wikipedia, at the web site addressed by en.wikipedia.org/wiki/Kalman_filter, the contents of which are incorporated by reference herein in its entirety. Software packages may be adapted for implementing the Kalman filter process with respect to image or other types of data.

Once the estimated registration parameters are obtained, these values may be applied to the reference image to update the alignment of the pre-operative planning image on the real-time patient image by using the updated estimated registration parameters. More specifically, the estimated registration parameter at time t is used to compute the positions of the image pixels or the control points of the reference image under the coordinate of the real-time patient image. Due to the use of the same coordinate, the image pixels at the reference image can be superimposed on the real-time patient image with the transformed positions. The process above may be repeated (e.g., periodically, continuously, or on-demand as appropriate) or may terminate.

Figure 5:
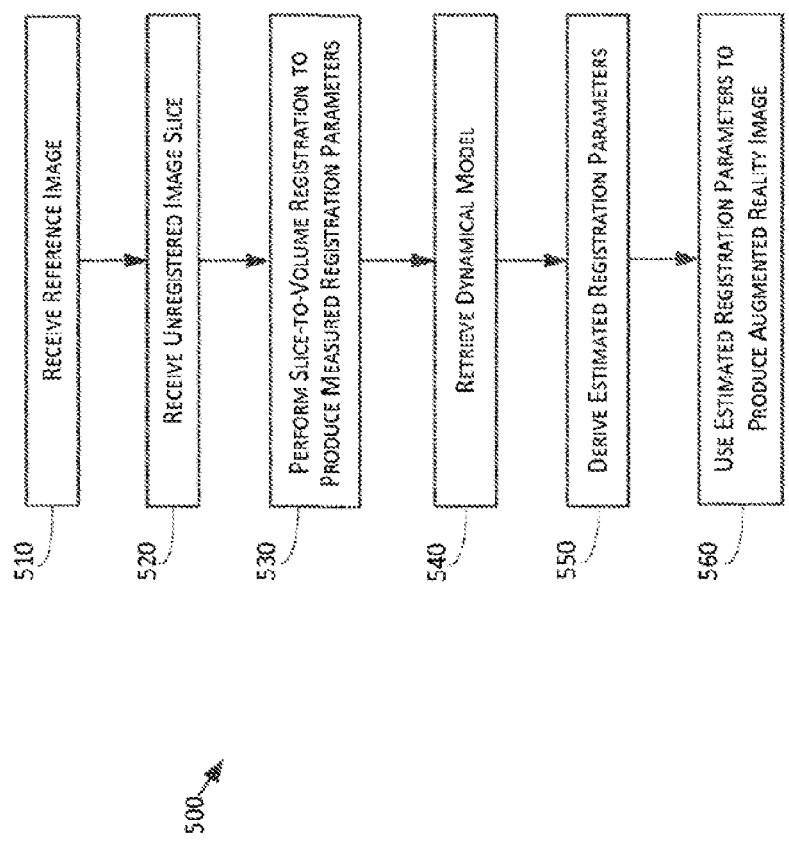
FIG. 5 is a flow diagram illustrating an example process for determining estimated registration parameters.

FIG. 5 is a flow diagram illustrating an example process 500 to determine estimated registration parameters, arranged in accordance with at least some embodiments presented herein. The process 500 may be performed by the imaging processing system 40 described previously. The process 500 may include various operations, functions, or actions as illustrated by one or more blocks 510-560. It should be appreciated that one or more blocks 510-560 may also be performed concurrently.

The process 500 may begin at block 510 (Receive Reference Image), where the imaging processing system 40 may receive a reference image. The reference image may be stored in a memory of the imaging processing system 40 or provided by a separate computing system. Block 510 may be followed by block 520.

At block 520 (Receive Unregistered Image Slice), the imaging processing system 40 may also receive an unregistered image slice. The imaging processing system 40 may receive the unregistered image slice simultaneously, before, or after receiving the reference image. Block 520 may be followed by block 530.

At block 530 (Perform Slice-to-Volume Registration to Produce Measured Registration Parameters), when both the reference image and the unregistered image have been obtained, the imaging processing system 40 may perform a slice-to-volume registration. The performance of the slice-to-volume registration may result in measured registration parameters. Block 530 may be followed by block 540.

At block 540 (Retrieve Dynamical Model), the imaging processing system 40 may retrieve the dynamical motion model. The dynamical motion model may describe the relevant organ motion and how the measured registration parameters may be obtained from the true registration parameters. The dynamical model may be stored in a memory of the imaging processing system 40 or provided by a separate computing system. Block 540 may be followed by block 550.

At block 550 (Derive Estimated Registration Parameters), the imaging processing system 40 may input the dynamical model, the measured registration parameters, and the estimated registration parameters at the previous time into a state estimation function to derive the estimated registration parameters at the current time in operation. Block 550 may be followed by block 560.

At block 560 (Use the Estimated Registration Parameters to Produce Augmented Reality Image), when the estimated registration parameters have been derived, the imaging processing system 40 may utilize the estimated registration parameters to compute the positions of the image pixels at the reference image under the coordinate of the real-time patient image. An augmented reality image can then be generated by superimposing the transformed image pixels of the reference image on the real-time patient image. After block 560, the process 500 may either repeat (e.g., periodically, continuously, or on demand as needed) with time or terminate.

Figure 6:
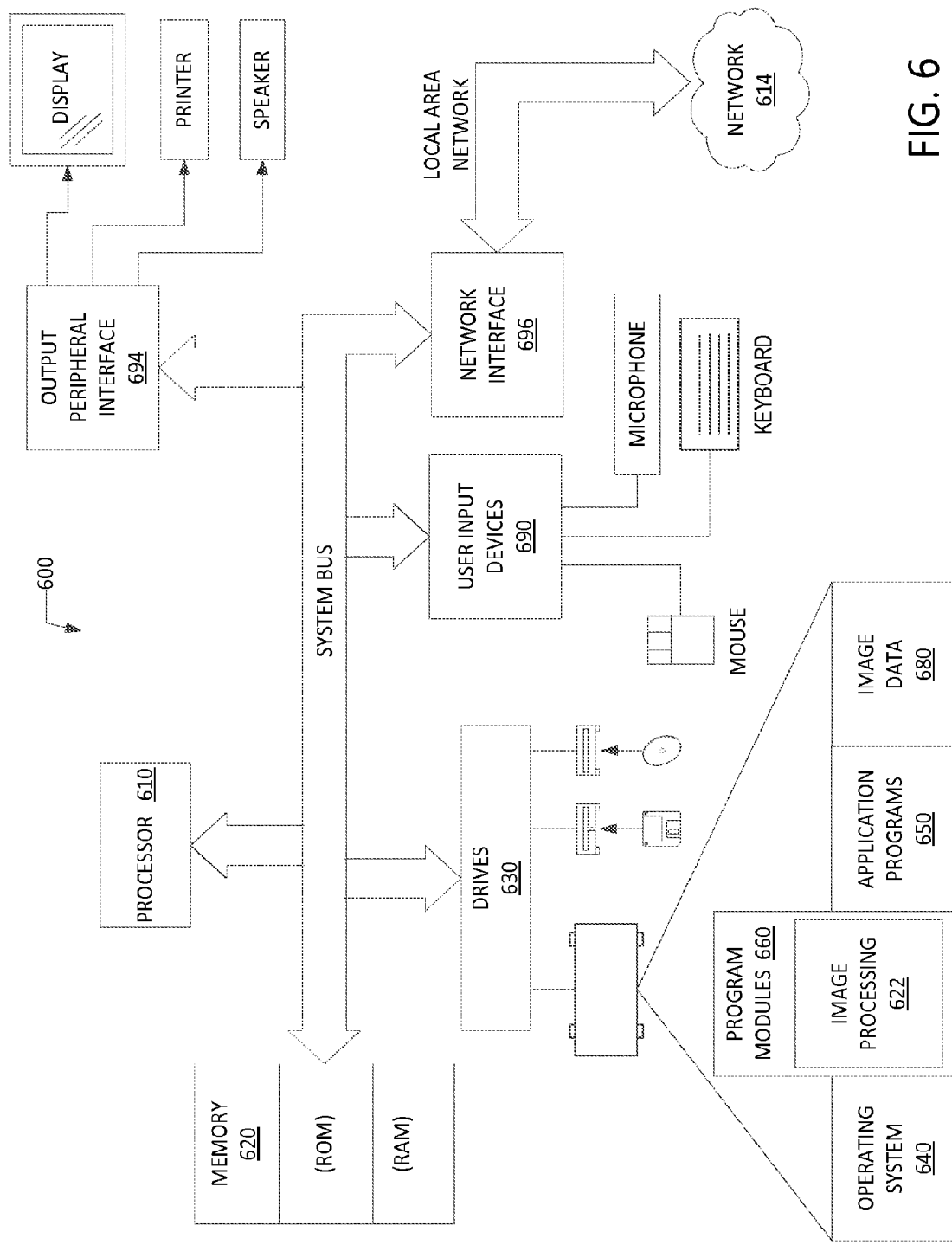
FIG. 6 is a block diagram of a computer architecture of an example computing system for determining the estimated registration parameters.

FIG. 6 is a block diagram of an example computer hardware architecture system, arranged in accordance with at least some embodiments presented herein. The computer 600 may illustrate a conventional server, desktop, or image processing computer, or image processing embedded system that can be utilized to execute any aspect of the methods presented herein. The computer 600 may be integrated with an imaging system, or can be a stand-alone image processing system receiving image data from the imaging system.

FIG. 6 includes a computer 600, including a processor 610, memory 620, and one or more storage drives 630. The computer 600 may be implemented as a conventional computer system, an embedded control computer, a laptop, or a server computer, a mobile device, or other type of hardware platform.

The drives 630 and their associated computer storage media, provide storage of computer readable instructions, data structures, program modules and other data for the computer 600. The drives 630 can include an operating system 640, application programs 650, program modules 660, and a database containing image data 680. Some examples of the program modules 660 may include an image processing module 622 that may include the slice-to-volume registration and/or state estimation operations using Kalman based filtering or other techniques to process the image data. The mass storage may also store the image data 680, which may include both the pre-operative planning data and real-time patient imaging data.

The computer 600 may further include user input devices 690 through which a user may enter commands and data. Input devices can include an electronic digitizer, a microphone, a keyboard and pointing device, commonly referred to as a mouse, trackball or touch pad. Other input devices may include a joystick, game pad, satellite dish, scanner, or the like.

These and other input devices can be coupled to the processor 610 through a user input interface that is coupled to a system bus, but may be coupled by other interface and bus structures, such as a parallel port, game port, or a universal serial bus ("USB"). The computer 600 may also include other peripheral output devices such as speakers, which may be coupled through an output peripheral interface 694 or the like.

The computer 600 may operate in a networked environment using logical connections to one or more computers, such as a remote computer coupled to a network interface 696. The remote computer may be a personal computer, a server, a router, a network PC, a peer device or other common network node, and can include many or all of the elements described above relative to the computer 600. Networking environments are commonplace in offices, enterprise-wide area networks ("WAN"), local area networks ("LAN"), intranets, and the Internet.

When used in a LAN or WLAN networking environment, the computer 600 may be coupled to the LAN through the network interface 696 or an adapter. When used in a WAN networking environment, the computer 600 typically includes a modem or other means for establishing communications over the WAN, such as the Internet or the network 614. The WAN may include the Internet, the illustrated network 614, various other networks, or any combination thereof. It will be appreciated that other mechanisms of establishing a communications link, ring, mesh, bus, cloud, or network between the computers may be used.

According to some embodiments, the computer 600 may be coupled to a networking environment. The computer 600 may include one or more instances of a physical computer-readable storage medium or media associated with the drives 630 or other storage devices. The system bus may enable the processor 610 to read code and/or data to/from the computer-readable storage media. The media may represent an apparatus in the form of storage elements that are implemented using any suitable technology, including but not limited to semiconductors, magnetic materials, optical media, electrical storage, electrochemical storage, or any other such storage technology. The media may represent components associated with memory 620, whether characterized as RAM, ROM, flash, or other types of volatile or nonvolatile memory technology. The media may also represent secondary storage, whether implemented as the storage drives 630 or otherwise. Hard drive implementations may be characterized as solid state, or may include rotating media storing magnetically-encoded information.

The storage media may include one or more program modules 660. The program modules 660 may include software instructions that, when loaded into the processor 610 and executed, transform a general-purpose computing system into a special-purpose computing system. As detailed throughout this description, the program modules 660 may provide various tools or techniques by which the computer 600 may participate within the overall systems or operating environments using the components, logic flows, and/or data structures discussed herein.

The processor 610 may be constructed from any number of transistors or other circuit elements, which may individually or collectively assume any number of states. More specifically, the processor 610 may operate as a state machine or finite-state machine. Such a machine may be transformed to a second machine, or specific machine by loading executable instructions contained within the program modules 660. These computer-executable instructions may transform the processor 610 by specifying how the processor 610 transitions between states, thereby transforming the transistors or other circuit elements constituting the processor 610 from a first machine to a second machine. The states of either machine may also be transformed by receiving input from the one or more user input devices 690, the network interface 696, other peripherals, other interfaces, or one or more users or other actors. Either machine may also transform states, or various physical characteristics of various output devices such as printers, speakers, video displays, or otherwise.

Encoding the program modules 660 may also transform the physical structure of the storage media. The specific transformation of physical structure may depend on various factors, in different implementations of this description. Examples of such factors may include, but are not limited to: the technology used to implement the storage media, whether the storage media are characterized as primary or secondary storage, and the like. For example, if the storage media are implemented as semiconductor-based memory, the program modules 660 may transform the physical state of the semiconductor memory 620 when the software is encoded therein. For example, the software may transform the state of transistors, capacitors, or other discrete circuit elements constituting the semiconductor memory 620.

As another example, the storage media may be implemented using magnetic or optical technology such as drives 630. In such implementations, the program modules 660 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. It should be appreciated that various other transformations of physical media are possible without departing from the scope and spirit of the present description.

Figure 7A:
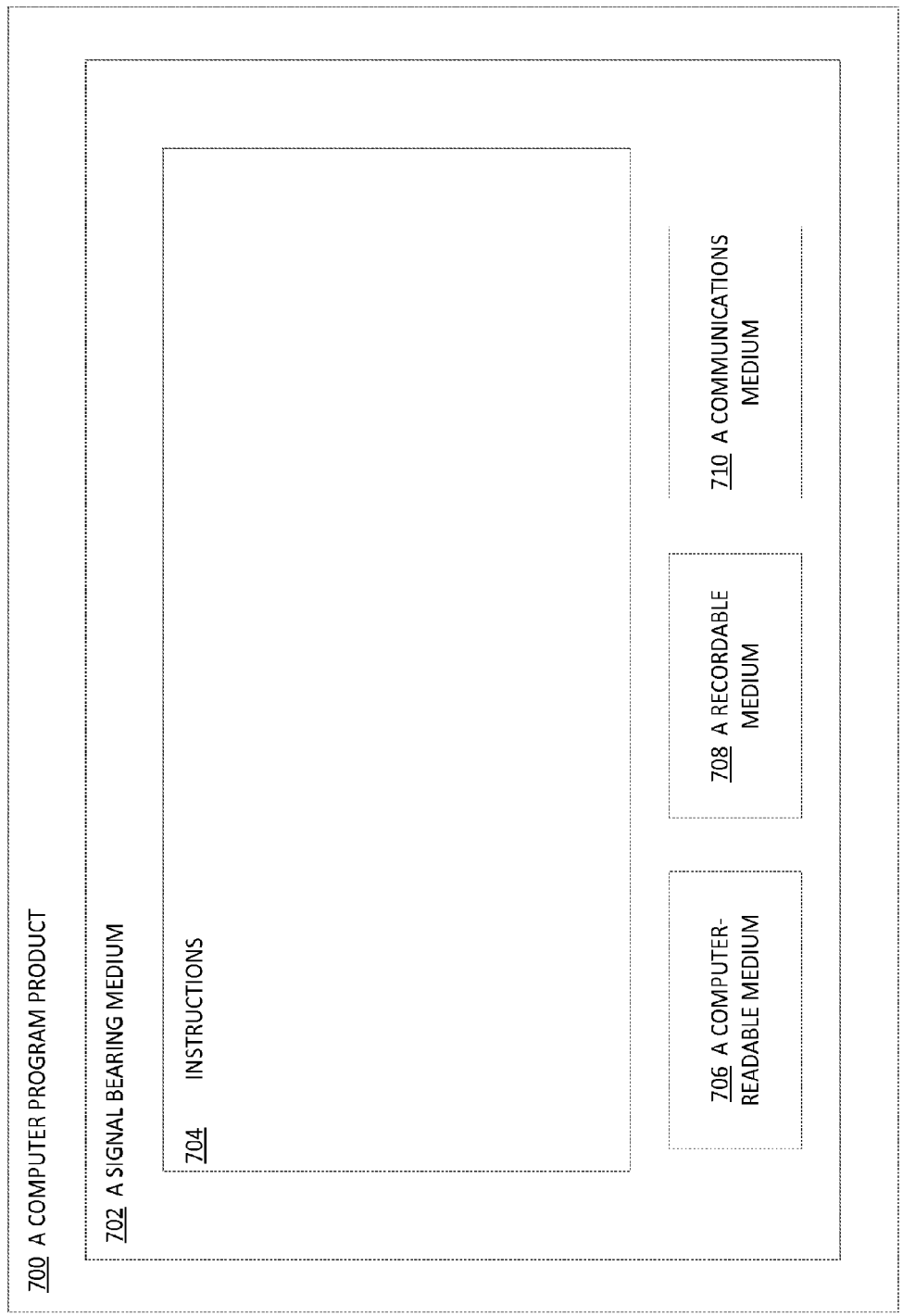

FIGS. 7A and 7B are schematic diagrams that illustrate a computer program product 700 that includes a computer program for executing a computer process on a computing device, arranged in accordance with at least some embodiments presented herein. An illustrative embodiment of the example computer program product is provided using a signal bearing medium 702, and may include at least one instruction of 704: one or more instructions for receiving a reference image of an organ of a patient from a first imaging modality device; one or more instructions for receiving a first unregistered image of the organ using a second imaging modality device or the first imaging modality device; one or more instructions for determining first measured registration parameters by registering the first unregistered image with the reference image; one or more instructions for determining predicted registration parameters for a second unregistered image using a dynamical model associated with motion of the organ; one or more instructions for determining second measured registration parameters of the second unregistered image by registering the second unregistered image with the reference image; one or more instructions for determining estimated registration parameters of the second unregistered image by using the predicted registration parameters to tune the second measured registration parameters; one or more instructions for registering the second unregistered image with the reference image using the estimated registration parameters; or one or more instructions for generating an augmented reality image comprising the reference image and the second image. In some embodiments, the signal bearing medium 702 of the one or more computer program products 700 includes a computer readable medium 706, a recordable medium 708, and/or a communications medium 710.

The above disclosure illustrates concepts and technologies for estimating the registration parameters associated with generating augmented reality images. The concepts and technologies disclosed herein are not limited to applications producing augmented images for surgical procedures, but can be used for other applications such as education or training purposes. The concepts can be applied to various applications where an augmented reality image is to be generated involving an objects exhibiting periodic movement that can be modeled.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, components, elements, apparatuses, or systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method to provide an augmented reality image, comprising:
  receiving a reference image of an organ of a patient from a first imaging modality device,
    wherein the reference image of the organ is a pre-operative planning image of the organ;
  receiving an unregistered image of the organ of the patient from a second imaging modality device or the first imaging modality device;
  determining predicted registration parameters for the unregistered image using a dynamical model associated with motion of the organ,
    wherein the dynamical model is characterized by a breathing motion model of the organ having as input the estimated registration parameters at a first time added to a noise value at a second time, and
    wherein the second time is after the first time;
  determining measured registration parameters of the unregistered image by a slice-to-volume registration of the unregistered image with the reference image;
  determining estimated registration parameters of the unregistered image by using the predicted registration parameters to tune the measured registration parameters;

registering the unregistered image with the reference image using the estimated registration parameters; and generating, by a computer, the augmented reality image comprising the reference image and the registered image.

2. The method of claim 1, further comprising:
causing the augmented reality image to be presented on a display.

3. The method of claim 2, further comprising:
receiving a second unregistered image of the organ of the patient using the second imaging modality device;
registering the second unregistered image of the organ with the reference image using the estimated registration parameters of the unregistered image;
generating an updated augmented reality image comprising the reference image and the second registered image; and
causing the updated augmented reality image to be presented on the display.

4. The method of claim 1, wherein the slice-to-volume registration defines a transformation of image pixels or control points in coordinate space from the unregistered image to the reference image.

5. The method of claim 1, wherein the first imaging modality device is different from the second imaging modality device.

6. The method of claim 1, wherein a Kalman filter process is used to determine the estimated registration parameters when a measurement function is linear and noise is a white Gaussian process with known mean and variances.

7. The method of claim 1, wherein an extended Kalman filter process is used to determine the estimated registration parameters when a measurement function is nonlinear and noise is a white Gaussian process with known mean and variances.

8. The method of claim 1, wherein an expectation-maximization process is used to determine the estimated registration parameters when noise is an unknown process.

9. The method of claim 1, wherein the unregistered image comprises a real-time image of the organ of the patient.

10. A system to provide an augmented reality image comprising:
a processor and a memory coupled to the processor;
an image generation module which executes in the processor from the memory and which, when executed by the processor, causes the processor to receive a reference image of an organ of a patient from a first imaging modality device,
receive an unregistered image of the organ of the patient from a second imaging modality device or the first imaging modality device,
determine predicted registration parameters for the unregistered image using a dynamical model associated with motion of the organ,
wherein the dynamical model is characterized by a breathing motion model of the organ having as input the estimated registration parameters at a first time added to a noise value at a second time, and
wherein the second time is after the first time,
determine measured registration parameters of the unregistered image by a slice to-volume registration of the unregistered image with the reference image,
determine estimated registration parameters of the unregistered image by using the predicted registration parameters to tune the measured registration parameters,
register the unregistered image with the reference image using the estimated registration; and
generate the augmented reality image comprising the reference image and the registered image.

11. The system of claim 10, wherein the unregistered image comprises a real-time image of the organ.

12. The system of claim 10, wherein the reference image of the organ comprises a three-dimensional image of the organ.

13. The system of claim 10, wherein the first imaging modality device is the same as the second imaging modality device.

14. The system of claim 10, wherein the image generation module, when executed by the processor, further causes the processor to perform operations of a Kalman filter to determine the estimated registration parameters when a measurement function is linear and noise is a white Gaussian process with known mean and variances.

15. The system of claim 10, wherein the image generation module, when executed by the processor, further causes the processor to perform operations of an extended Kalman filter process to determine the estimated registration parameters when a measurement function is nonlinear and noise is a white Gaussian process with known mean and variances.

16. The system of claim 10, wherein the image generation module, when executed by the processor, further causes the processor to use an expectation-maximization method to determine the estimated registration parameters when noise is an unknown process.

17. A non-transitory computer-readable medium having computer-executable instructions stored thereon which, when executed by a computer, cause the computer to:
receive a reference image of an organ of a patient from a first imaging modality device;
receive an unregistered image of the organ of the patient from a second imaging modality device or the first imaging modality device;
determine predicted registration parameters for the unregistered image using a dynamical model associated with motion of the organ,
wherein the dynamical model is characterized by a breathing motion model of the organ having as input the estimated registration parameters at a first time added to a noise value at a second time, and
wherein the second time is after the first time;
determine measured registration parameters of the unregistered image by a slice-to volume registration of the unregistered image with the reference image;
determine estimated registration parameters of the unregistered image by using the predicted registration parameters to tune the measured registration parameters;
register the unregistered image with the reference image using the estimated registration parameters; and
generate an augmented reality image comprising the reference image and the registered lmage.

18. The non-transitory computer-readable medium of claim 17, wherein a Kalman filter process is used to determine the estimated registration parameters when a measurement function is linear and noise is a white Gaussian process with known mean and variances.

19. The non-transitory computer-readable medium of claim 17, wherein an extended Kalman filter process is used to determine the estimated registration parameters when a measurement function is nonlinear and noise is a white Gaussian process with known mean and variances.

20. The non-transitory computer-readable medium of claim 17, wherein an expectation-maximization process is used to determine the estimated registration parameters when noise is an unknown process.

* * * * *